(12) United States Patent
Smith et al.

(10) Patent No.: US 9,974,530 B2
(45) Date of Patent: May 22, 2018

(54) TISSUE SECURING AND SEALING APPARATUS AND RELATED METHODS OF USE

(71) Applicant: Boston Scientific Scimed, Inc., Maple Grove, MN (US)

(72) Inventors: Paul J. Smith, Smithfield, RI (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 327 days.

(21) Appl. No.: 14/820,301

(22) Filed: Aug. 6, 2015

(65) Prior Publication Data

US 2015/0342638 A1 Dec. 3, 2015

Related U.S. Application Data

(63) Continuation of application No. 12/153,369, filed on May 16, 2008, now Pat. No. 9,125,631.

(60) Provisional application No. 60/924,496, filed on May 17, 2007.

(51) Int. Cl.
| | | |
|---|---|---|
| *A61B 17/10* | (2006.01) | |
| *A61B 17/00* | (2006.01) | |
| *A61B 17/34* | (2006.01) | |
| *A61B 17/02* | (2006.01) | |
| A61B 17/30 | (2006.01) | |
| A61B 90/00 | (2016.01) | |

(52) U.S. Cl.
CPC .... *A61B 17/00234* (2013.01); *A61B 17/0218* (2013.01); *A61B 17/3423* (2013.01); *A61B 17/3478* (2013.01); *A61B 2017/00278* (2013.01); *A61B 2017/00292* (2013.01); *A61B 2017/00862* (2013.01); *A61B 2017/306* (2013.01); *A61B 2017/3488* (2013.01); *A61B 2090/034* (2016.02)

(58) Field of Classification Search
CPC .......... A61B 17/00234; A61B 17/0218; A61B 17/3423; A61B 17/3478; A61B 2017/00278; A61B 2017/00292; A61B 2017/00862; A61B 2017/306; A61B 2017/3488; A61B 2090/034; A61B 2017/12018; A61B 17/12013; A61B 17/11
USPC ................... 604/164.01, 174, 164.09, 164.1; 606/139, 140, 141, 185, 192
See application file for complete search history.

(56) References Cited

U.S. PATENT DOCUMENTS

| | | |
|---|---|---|
| 5,297,536 A | 3/1994 | Wilk |
| 5,320,630 A | 6/1994 | Ahmed |
| 5,697,940 A | 12/1997 | Chu et al. |

(Continued)

FOREIGN PATENT DOCUMENTS

| | | |
|---|---|---|
| EP | 0 745 350 A1 | 12/1996 |
| WO | WO 94/15655 A2 | 7/1994 |
| WO | WO 97/32528 A1 | 9/1997 |

OTHER PUBLICATIONS

International Search Report for corresponding PCT Application No. PCT/US2008/063910 dated Mar. 19, 2009.

(Continued)

*Primary Examiner* — Katherine M Shi
(74) *Attorney, Agent, or Firm* — Bookoff McAndrews, PLLC

(57) ABSTRACT

Embodiments of the invention may be directed to apparatuses for securing and sealing tissue and related methods of use.

15 Claims, 10 Drawing Sheets

(56) References Cited

U.S. PATENT DOCUMENTS

| | | | |
|---|---|---|---|
| 6,059,816 | A | 5/2000 | Moenning |
| 6,235,040 | B1 | 5/2001 | Chu et al. |
| 6,743,207 | B2 | 6/2004 | Elbert et al. |
| 2002/0038077 | A1 | 3/2002 | De la Torre et al. |
| 2002/0103495 | A1 | 8/2002 | Cole |
| 2002/0165553 | A1* | 11/2002 | Elbert ............... A61B 17/3415 606/108 |
| 2003/0158563 | A1 | 8/2003 | McClellan et al. |
| 2003/0208153 | A1 | 11/2003 | Stenzel |
| 2004/0097973 | A1* | 5/2004 | Loshakove ........ A61B 17/0644 606/144 |
| 2004/0122349 | A1 | 6/2004 | Lafontaine et al. |
| 2004/0147866 | A1 | 7/2004 | Blatter et al. |
| 2005/0192604 | A1* | 9/2005 | Carson ................. A61B 17/11 606/153 |
| 2006/0116749 | A1 | 6/2006 | Willink et al. |
| 2007/0135825 | A1 | 6/2007 | Binmoeller |
| 2007/0260112 | A1 | 11/2007 | Rahmani |
| 2008/0097478 | A1 | 4/2008 | Doughty et al. |
| 2008/0188863 | A1 | 8/2008 | Chu |

OTHER PUBLICATIONS

Written Opinion for International Search Authority for corresponding PCT/US2008/063910 dated Mar. 19, 2009.
Communication Relating to the Results of the Partial International Search in PCT/US2008/063910 (Annex to PCT/ISA/206—Invitation to Pay Additional Fees dated Nov. 21, 2008), 4 pages.

* cited by examiner

TISSUE SECURING AND SEALING APPARATUS AND RELATED METHODS OF USE

CROSS-REFERENCE TO RELATED APPLICATIONS

This patent application is a Continuation of U.S. patent application Ser. No. 12/153,369, filed May 16, 2008, which claims the benefit of priority under 35 U.S.C. § 119 to U.S. Provisional Patent Application No. 60/924,496, filed May 17, 2007, all of which are incorporated herein by reference in their entirety.

DESCRIPTION OF THE INVENTION

Field of the Invention

Embodiments of the invention may be directed to apparatuses for securing and sealing tissue and related methods of use.

Background of the Invention

Medical devices and procedures are used to treat internal body organs of a patient. One method of treating internal body organs includes open surgery where the internal body organs are exposed to the outside environment. Such procedures are invasive, expensive, time consuming, and may have a high risk of infection.

Another method includes laparoscopic procedures where punctures are made on the external surface of the body and medical devices are advanced into body cavities via the punctures. A laparoscope is used in conjunction with the medical devices to view the treatment of the internal body organs via the medical devices. While less invasive then open surgery, there are still contamination risks, primarily due to the direct exposure of the punctures to the outside environment.

SUMMARY OF THE INVENTION

An embodiment of the invention may include an apparatus. The apparatus may include an outer housing defining a first lumen, an elongate member defining a second lumen, the elongate member being configured to be disposed in the first lumen, and a securing mechanism configured to secure tissue around a distal portion of the elongate member. The elongate member and the outer housing may be longitudinally moveable relative to each other.

Various embodiments of the invention may include one or more of the following aspects: an elongate assembly configured to be disposed in the second lumen; the elongate assembly may include a distal portion configured to form a perforation in tissue; a dilation portion configured to expand the perforation; a guidewire; the elongate assembly may define a lumen configured to accommodate the guidewire therethrough; the distal portion and the dilation portion may be longitudinally moveable relative to each other; the distal portion and the dilation portion may be longitudinally fixed relative to each other; a distal portion of the outer housing may be configured to accommodate the securing mechanism for deployment of the securing mechanism around the distal portion of the elongate member; the outer housing may be configured to accommodate suction through the first lumen; and the securing mechanism may be an elastic band disposed in a tensioned state around a distal portion of the outer housing; the securing mechanism may be configured to form a substantially fluid-tight seal between the tissue and the distal portion of the elongate member.

Another embodiment of the invention may include an apparatus. The apparatus may include an elongate member defining a lumen, an elongate assembly configured to be disposed in the lumen, the elongate assembly and the elongate member longitudinally moveable relative to each other, and a securing mechanism configured to secure tissue around a distal portion of the elongate member.

Various embodiments of the invention may include one or more of the following aspects: the elongate assembly may include a distal portion configured to form a perforation in tissue; a dilation portion configured to expand the perforation; the dilation portion and the distal portion may be longitudinally moveable relative to each other; in a first configuration the dilation portion may be configured to substantially surround the distal portion, and in a second configuration the distal portion may be exposed; a guidewire; the elongate assembly may define a lumen configured to accommodate the guidewire therethrough; the distal portion and the dilation portion may be longitudinally fixed relative to each other; the dilation portion include a balloon; the dilation portion may include one of a stent, a cage, a basket, a forceps, and a scissors-like device; when the balloon is in an inflated configuration, the balloon may have a cross-sectional area greater than or equal to a cross-sectional area of the lumen of the elongate member; when the balloon is in an inflated configuration, the balloon may have a cross-sectional area smaller than a cross-sectional area of the elongate member; the elongate assembly may include a stop mechanism configured to limit movement of the dilation portion; the securing mechanism may be configured to form a substantially fluid-tight seal between the tissue and the distal portion of the elongate member; an outer housing defining a another lumen; the elongate member may be configured to be disposed in the another lumen; the elongate member and the outer housing may be longitudinally moveable relative to each other; a distal portion of the outer housing may be configured to accommodate the securing mechanism for deployment of the securing mechanism around the distal portion of the elongate member; and the outer housing may be configured to accommodate suction through the another lumen of the outer housing.

A further embodiment of the invention may include a method. The method may include advancing an outer housing defining a first lumen through a body lumen, advancing an elongate member defining a second lumen through the first lumen, forming a perforation in a wall of the body lumen, advancing a distal portion of the elongate member through the perforation, and securing body tissue surrounding the perforation to the distal portion of the elongate member with a securing mechanism.

Various embodiments of the invention may include one or more of the following aspects: advancing the securing mechanism from the outer housing to the body tissue surrounding the distal portion of the elongate member so as to secure the body tissue to the distal portion of the elongate member; contracting the securing mechanism around the body tissue surrounding the distal portion of the elongate member so as to secure the body tissue to the distal portion of the elongate member; advancing an elongate assembly through the second lumen; the perforation may be formed by a distal portion of the elongate assembly; retracting the elongate assembly from the second lumen; advancing a medical device through the second lumen; advancing a guidewire through a lumen defined by the elongate assembly; the securing mechanism may be an elastic band; sealing the body tissue surrounding the perforation to the distal portion of the elongate member with the securing mechanism; pulling body tissue into the first lumen; securing body tissue surrounding the perforation to the distal portion of the elongate member with the securing mechanism may include securing the body tissue pulled into the first lumen to the distal portion of the elongate member with the securing mechanism; advancing a medical device through the second lumen, through the perforation, and to a location outside of the body lumen; and performing a medical procedure with the medical device at the location outside of the body lumen.

Yet another embodiment of the invention may include a method. The method may include advancing an elongate assembly into a body lumen, the elongate assembly including a distal portion and a dilation portion, forming a perforation in a wall of the body lumen by piercing the wall with the distal portion, advancing the dilation portion into the perforation, expanding the perforation by activating the dilation portion, after the step of expanding the perforation, advancing a distal portion of an elongate member defining a lumen into the perforation, and securing body tissue surrounding the perforation to the distal portion of the elongate member with a securing mechanism.

Various embodiments of the invention may include one or more of the following aspects: advancing a guidewire through a lumen defined by the distal assembly and out a distal end of the distal portion; the elongate assembly may be advanced through the lumen of the elongate member; preventing the dilation portion from extending distally past the distal portion; longitudinally moving the dilation portion and the distal portion relative to each other; positioning an outer housing over the elongate assembly proximate the perforation; moving the securing mechanism from the outer housing to the body tissue surrounding the distal portion of the elongate member so as to secure the body tissue to the distal portion of the elongate member; the securing mechanism may be disposed on an outer surface of the outer housing prior to moving the securing mechanism from the outer housing to the body tissue surrounding the distal portion of the elongate member so as to secure the body tissue to the distal portion of the elongate member; contracting the securing mechanism around the body tissue surrounding the distal portion of the elongate member so as to secure the body tissue to the distal portion of the elongate member; sealing the body tissue surrounding the perforation to the distal portion of the elongate member with the securing mechanism; pulling body tissue into a lumen defined by an outer housing; securing body tissue surrounding the perforation to the distal portion of the elongate member with the securing mechanism may include securing the body tissue pulled into the lumen defined by the outer housing to the distal portion of the elongate member with the securing mechanism; advancing a medical device through the lumen of elongate member, through the perforation, and into a location outside of the body lumen; and after the step of advancing the medical device through the lumen of the elongate member and the perforation, performing a medical procedure with the medical device at the location outside of the body lumen.

A yet further embodiment of the invention may include an apparatus. The apparatus may include an outer housing defining a lumen, a lip disposed on a distal end of the outer housing and configured to accommodate tissue thereon, the lip having a cross-sectional area smaller than a cross-sectional area of the outer housing adjacent to the lip, and a securing mechanism configured to secure tissue around the lip.

Various embodiments of the invention may include one or more of the following aspects: an elongate assembly configured to be disposed in the lumen; the elongate assembly may include a distal portion configured to form a perforation in tissue; a dilation portion configured to expand the perforation; the securing mechanism may be an elastic band disposed around a portion of the outer housing adjacent to the lip; and the securing mechanism may be configured to form a substantially fluid-tight seal between the tissue and the lip.

Another embodiment of the invention may include an apparatus. The apparatus may include an elongate assembly having a distal portion configured to form a perforation in tissue, and a dilation portion configured to expand the perforation.

In some embodiments, the dilation portion may be slideable relative to an external surface of the elongate assembly; and the dilation portion may include a balloon fixed to the elongate assembly, and the distal portion may include a sharp portion fixed to the elongate assembly.

A further embodiment of the invention may include a method. The method may include providing a first elongate member proximate an aperture in a wall of tissue, wherein the first elongate member includes a lumen and a securing mechanism, providing a second elongate member disposed within the lumen of the first elongate member and extending through the aperture, pulling tissue surrounding the aperture toward the first elongate member, and deploying the securing mechanism about the tissue surrounding the aperture to secure the tissue surrounding the aperture to the second elongate member.

Various embodiments of the invention may include one or more of the following aspects: the step of pulling the tissue may include suctioning the tissue; the step of pulling the tissue surrounding the aperture toward the first elongate member may include pulling tissue into the lumen of the first elongate member; and the method may further include pulling the second elongate member out of the aperture so that the securing member closes the aperture.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
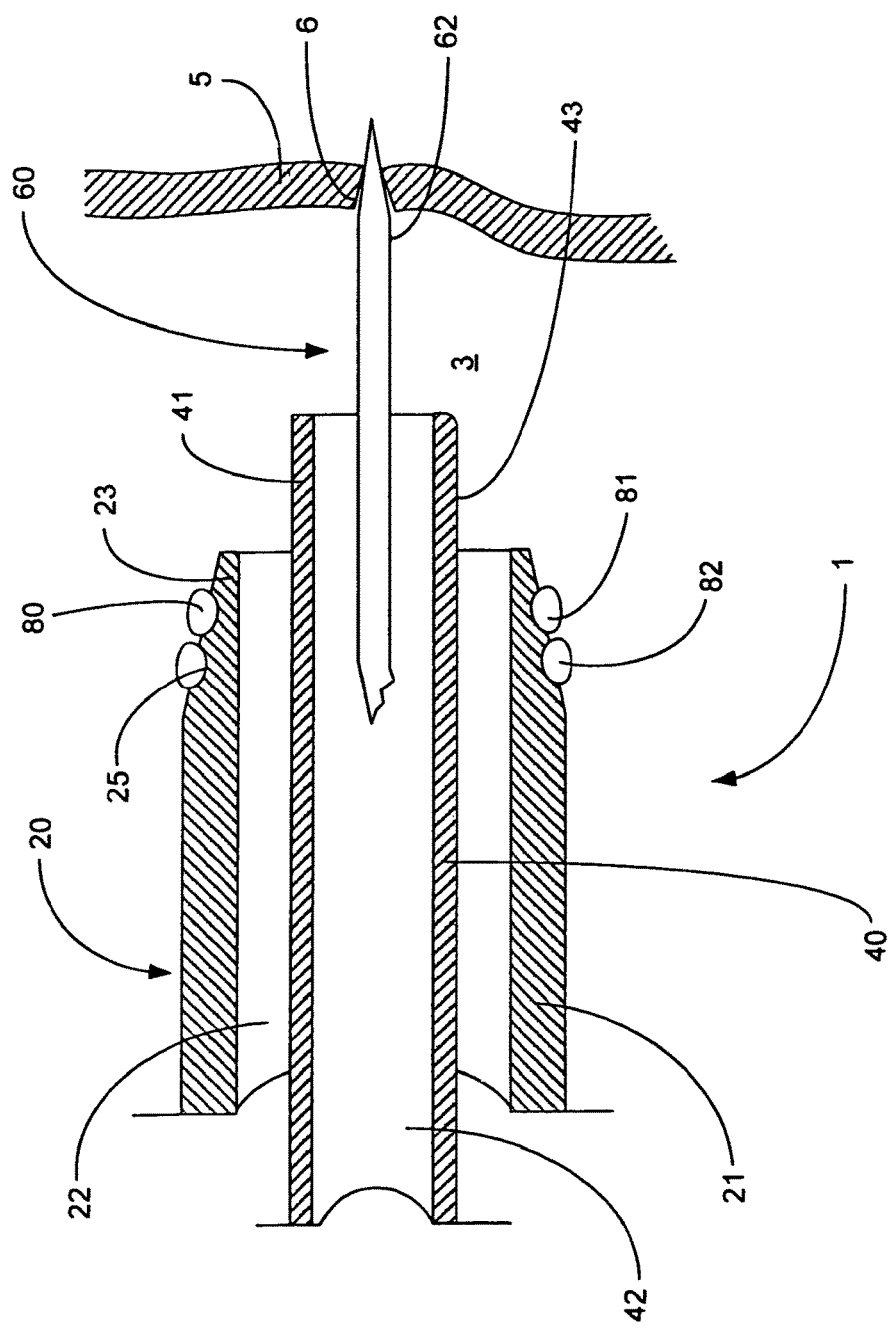
FIGS. 1-6, 6A, 6B depict an apparatus and method of using the apparatus, according to an exemplary embodiment of the invention.

Reference will now be made in detail to exemplary embodiments of the invention, examples of which are illustrated in the accompanying drawings. Wherever possible, the same reference numbers will be used throughout the drawings to refer to the same or like parts.

An embodiment of invention includes an apparatus 1, which is depicted in FIGS. 1-6, 6A, 6B. Apparatus 1 may include an outer housing 20, an elongate member 40 disposed in outer housing 20, an elongate assembly 60, and securing mechanism 80.

Examples of various portions of outer housing 20 are shown in FIGS. 1-6, 6A, 6B. Outer housing 20 may include an elongate member 21 defining a lumen 22. Elongate member 21 may be configured to be advanced through a body lumen, for example, a gastrointestinal tract ("GI tract 3") of a patient. Other examples of body lumens that may be suitable for use in connection with embodiments of the present invention, including a vaginal tract, vascular tract, urinary tract, and/or biliary tract. Elongate member 21 may be configured to be advanced through lumen 4 of an endoscope 2, or any other suitable medical device. At least some portions of elongate member 21 may be flexible, for example, so as to allow elongate member 21 to traverse tortuous anatomy. A distal portion 23 of outer housing 20 may be configured to accommodate and/or actuate securing mechanism 80. For example, outer surface of distal portion 23 may taper radially inward as one moves distally along outer housing 20. Outer housing 20 may be an endoscope, a portion of an endoscope, and/or be attached to or slideable within an endoscope.

Figure 6:
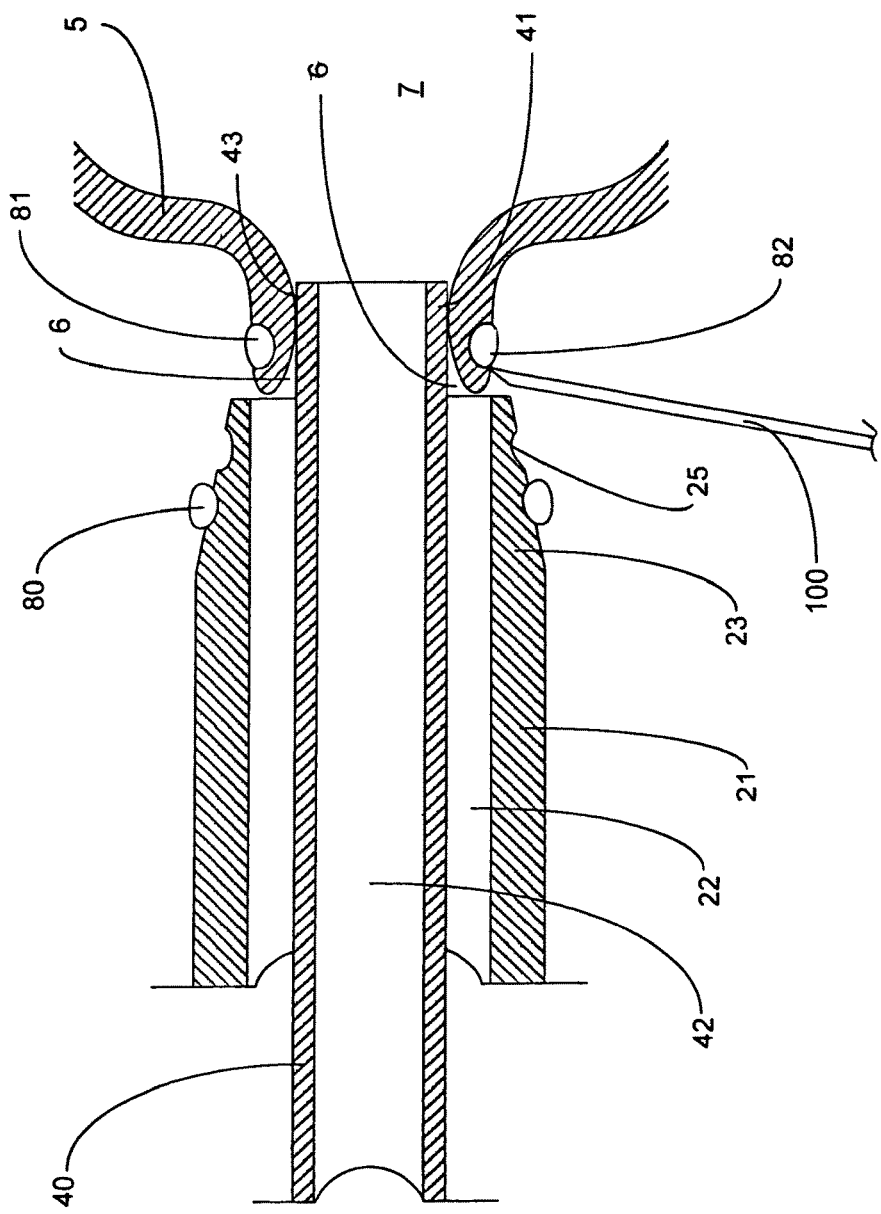
Figure 6A:
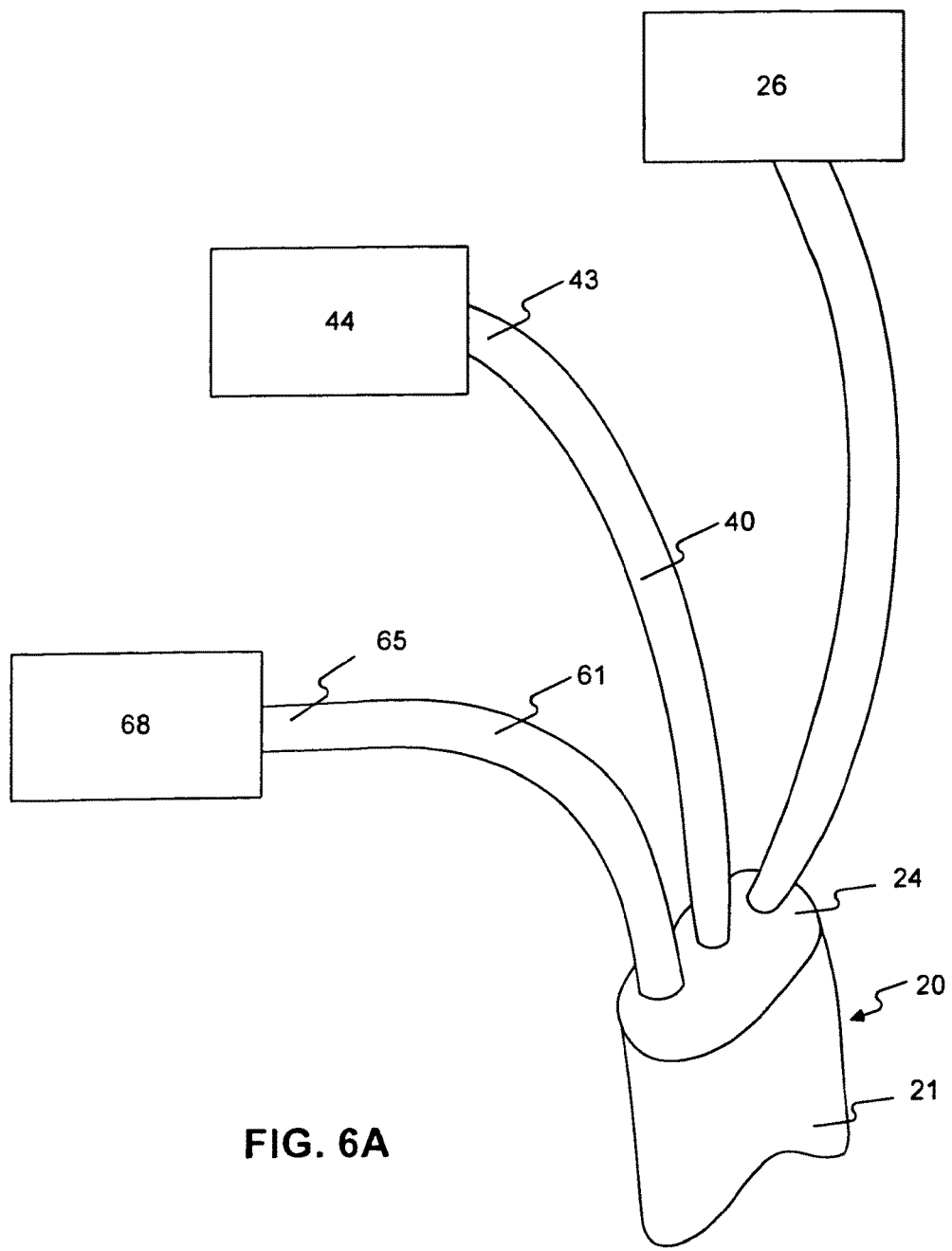

Lumen 22 may extend at least along a portion of outer housing 20, and may be configured to accommodate one or more medical devices therethrough, for example, elongate member 40 and/or elongate assembly 60. Lumen 22 may also be configured to accommodate irrigation and/or aspiration therethrough. To that end, a proximal portion 24 of outer housing 20 may be connected to a source of fluid or suction (or other means of otherwise pulling tissue) 26 that is in flow communication with lumen 22, as shown in FIG. 6A. FIG. 6A shows an exemplary embodiment of the proximal portions of apparatus 1. Source of suction 26 may provide sufficient suction, for example, to draw a portion of tissue wall 5 into a distal opening of housing 20 and a portion of lumen 22 defined by distal portion 23 when elongate member 40 is disposed within a tissue perforation 6. Source 26 or proximal end 24 may also include any other suitable handle/actuation structure for operation of housing 20 and actuation or placement of securing mechanism 80. Examples of such operations may include releasing securing mechanism 80 from outer housing 20, articulating a flexible section of outer housing 20, stiffening a flexible section of outer housing 20, and/or performing any of aspiration, irrigation, suction, and insufflation.

Figure 6B:
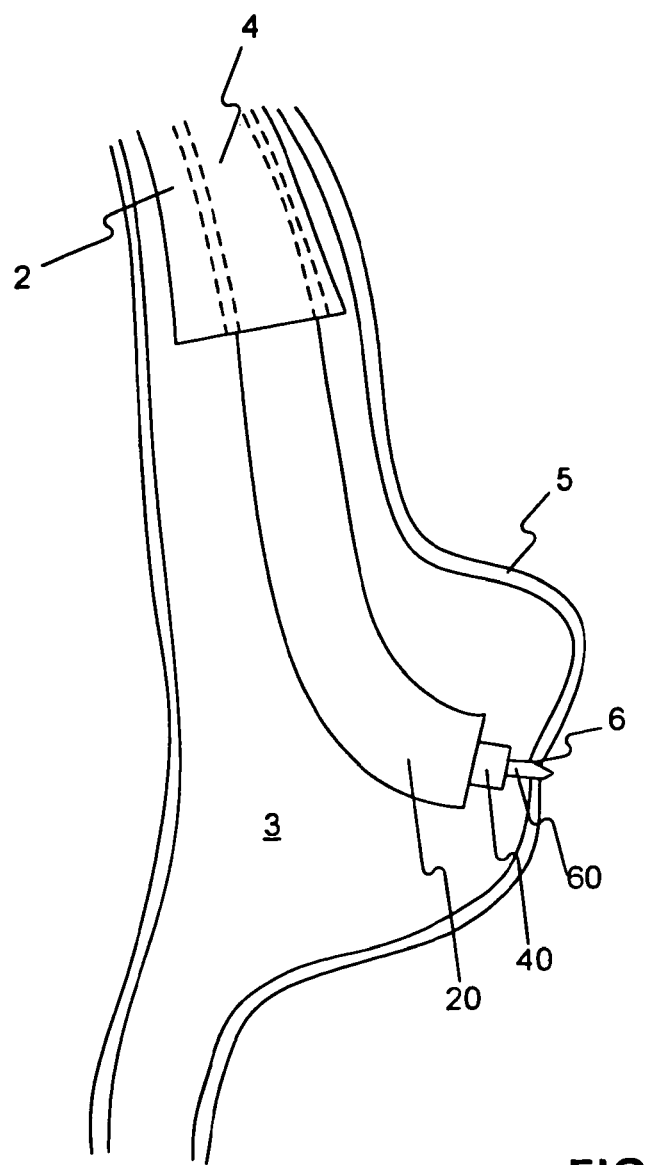

Examples of various portions of elongate member 40 are shown in FIGS. 1, 6A, 6B. Elongate member 40 may be configured to advance through a body lumen, for example, GI tract 3. Elongate member 40 may also be configured to be advanced through lumen 4 of endoscope 2, lumen 22 of outer housing 20, and/or any other suitable medical device. At least some portions of elongate member 40 may be flexible, for example, so as to allow elongate member 21 to traverse tortuous anatomy. Additionally, elongate member 40 may have any suitable length, for example, elongate member 40 may extend distally and/or proximally past at least one end of outer housing 20.

A distal portion 41 of elongate member 40 may be configured to be advanced through tissue, for example, a wall 5 of GI tract 3 that separates GI tract 3 from a body cavity 7. Distal portion 41 may have a taper to allow it to be more easily placed through perforation 6. Distal portion 41 may also be configured to allow tissue to be secured therearound, for example, wall 5 of GI tract 3 by securing mechanism 80. Furthermore, distal portion 41 may define an opening in fluid communication with lumen 42 described below. In some embodiments, the opening may be selectively and/or partially closed to, for example, prevent contamination of lumen 42. The opening may be selectively and/or partially closed by any suitable means known in the art. For example, the opening may be covered by a readily removable (penetratable) membrane (not shown) that covers all or part of the opening. In another example, the annulus of the opening may be configured to elastically open and close.

In some embodiments, distal portion 41 may be provided with a substantially atraumatic distal tip. Alternatively, distal portion 41 may be configured to pierce tissue, for example, wall 5 of GI tract 3. Distal portion 41 may be configured to pierce tissue using any suitable means known in the art, for example, distal portion 41 may be a knife and/or include a sharp tip configured to itself pierce tissue or include a source of energy configured to focus and/or pierce tissue, such as, for example, heat, laser, infrared, ultrasound, or any other suitable type of energy.

Elongate member 40 may define lumen 42, which may extend at least partially therethrough. Lumen 42 may be configured to accommodate advancement of one or more medical devices therethrough, for example, elongate assembly 60. Lumen 42 may also be configured to accommodate irrigation, aspiration, suction and/or pneumatics therethrough. To that end, a proximal portion 43 of elongate member 40 may be connected to a source of fluid or suction 44 that is in flow communication with lumen 42. Source 44 may also include any other suitable handle/actuation structure for operation of elongate member 40. Examples of such operations may include articulating a flexible section of elongate member 40, stiffening a flexible section of elongate member 40, and/or performing any of aspiration, irrigation, suction, and insufflation.

A portion, such as, for example, distal portion 41, of elongate member 40 may further include a dilating member (not shown). The dilating member may be configured to expand to any desired size by any suitable means known in the art. For example, the dilating member may be a balloon that is configured to inflate. Alternatively, the dilating member may include an expandable stent or cage having suitable scaffolding for structural support. The dilating member may further include a scissors-like device, such as, for example, forceps.

In various embodiments, elongate member 40 may include any number of aspects. For example, elongate member 40 may include an obturator. Elongate member 40 may be configured to maintain a seal with wall 5 of GI tract 3, may be configured to maintain a sterile or septic path for medical instruments, and/or may be sized to incorporate or pass tools therethrough. Elongate member 40 may include a bioabsorbable plug. Distal portion 41 of elongate member 40 may include a surface/textured finish and/or one or more grooves configured to aid in securing securing mechanism 80 thereto. A portion (e.g., distal portion 41) of elongate member 40 may be provided with one or more agents. Those having ordinary skill in the art will readily recognize that the term "agents" includes, but is not limited to, therapeutic agents, sterilizing agents, agents that facilitate entry and withdrawal of distal portion 41 into and from perforation 6, and/or agents that promote creating a seal between portions of wall 5 and distal portion 41. In some embodiments, the agents may include hydrophilic compounds, pharmacological compounds, polymers, and/or foam. The agents may be provided to distal portion 41 by any suitable means known in the art. For example, a surface of distal portion 41 may be coated or covered with any suitable, desired agent. Alternatively, the material that comprises distal portion 41 may be impregnated with a desired agent.

Examples of various portions of elongate assembly 60 are shown in FIGS. 1-4 and 6A. Elongate assembly 60 may include an elongate member 61, a distal portion 62, and a dilation portion 63. Elongate assembly 60 may be configured to be advanced through one or more lumens of one or more medical devices, for example, lumen 22 of outer housing 20 and lumen 42 of elongate member 40. Elongate assembly 60 may be configured to be advanced through a body lumen, for example, GI tract 3. Elongate member 61 may define a lumen 64 configured to accommodate fluid flow therethrough, for example, suction or irrigation of any suitable liquid or gas. Lumen 64 may be configured to accommodate a medical instrument therethrough, for example, a guidewire, cautery probe, or needle knife. A proximal portion 65 of elongate member 61 may connect to a source of fluid (liquid or gas) 68 in flow communication with lumen 64. Source 68 may alternatively or additionally be a source of suction or energy. Source 68 may also include other suitable handle/actuation structure for operation of elongate assembly 60, including inflation of dilation portion 63. Other examples of operations may include articulating a flexible section of elongate assembly 60, stiffening a flexible section of elongate assembly 60, actuating a source of energy, and/or performing any of aspiration, irrigation, suction, and insufflation.

Distal portion 62 may be configured to pierce tissue, for example, wall 5 of GI tract 3. Distal portion 62 may be configured to pierce tissue using any suitable method, for example, distal portion 62 may be a knife and/or include a sharp tip configured to itself pierce tissue or include a source of energy configured to focus and/or pierce tissue, such as heat, laser, infrared, or any other suitable type of energy. Distal portion 62 may be configured to pierce tissue to create a perforation of any suitable size, for example, to create a perforation 6 configured to allow distal portion 41 of elongate member 40 and/or dilation portion 63, either dilated or undilated, to be advanced therethrough.

Dilation portion 63 may be configured to expand perforation 6 to any desired size by any suitable means known in the art. For example, dilation portion 63 may include any suitable mechanical dilation system known in the art. Additionally, dilation portion 63 may be activated by any suitable means known in the art. In some embodiments, dilation portion 63 may include a balloon that is configured to inflate. Alternatively, dilation portion 63 may include an expandable stent, cage, basket or scissors-like device, as discussed above in connection with distal portion 41. In some embodiments, dilation portion 63 may be provided with one or more cutting means around a periphery of dilation portion 63. For example, in embodiments where dilation portion 63 is configured as an inflatable balloon, dilation portion 63 may be provided with blades and/or razors disposed about a periphery of the balloon. An example of such a device includes the Flextome® Cutting Balloon® Dilatation Device marketed by Boston Scientific Corporation.

Figure 2:
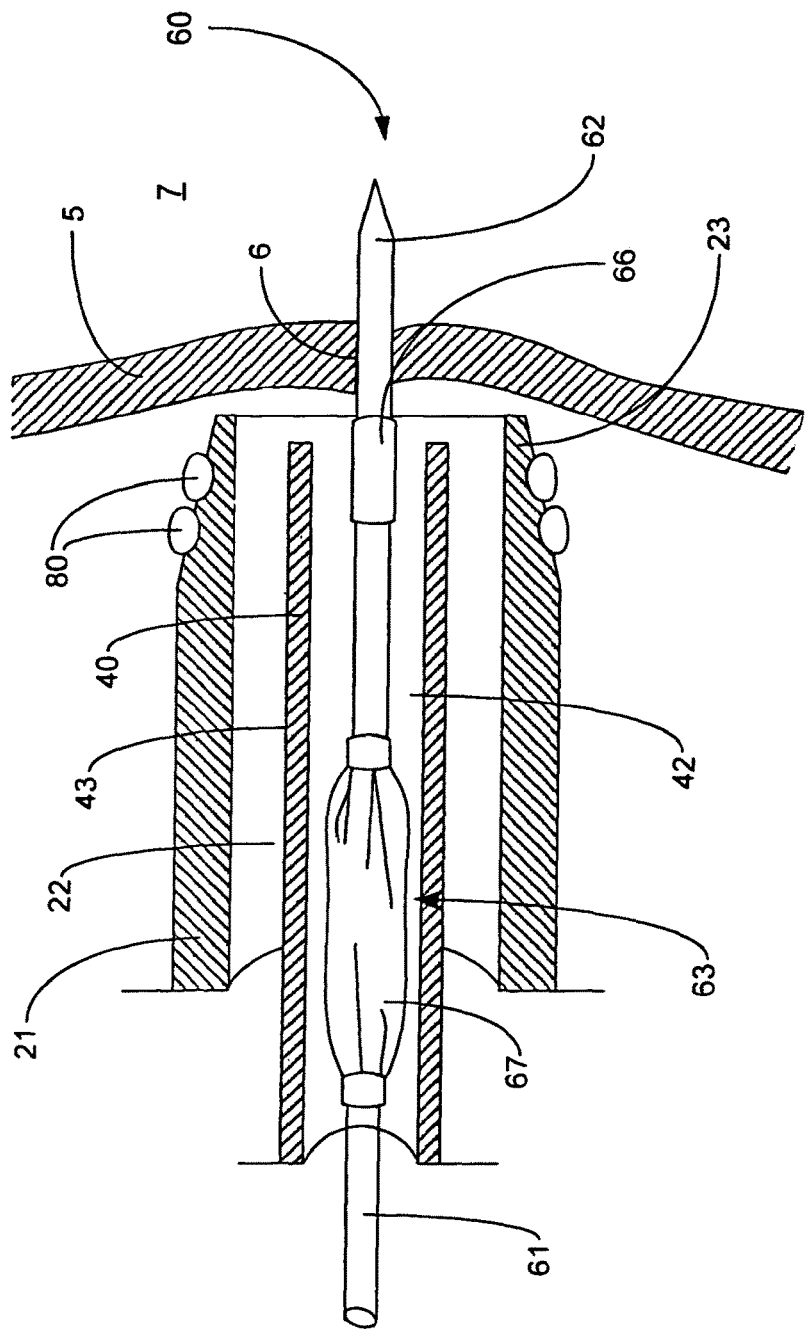
Figure 3:
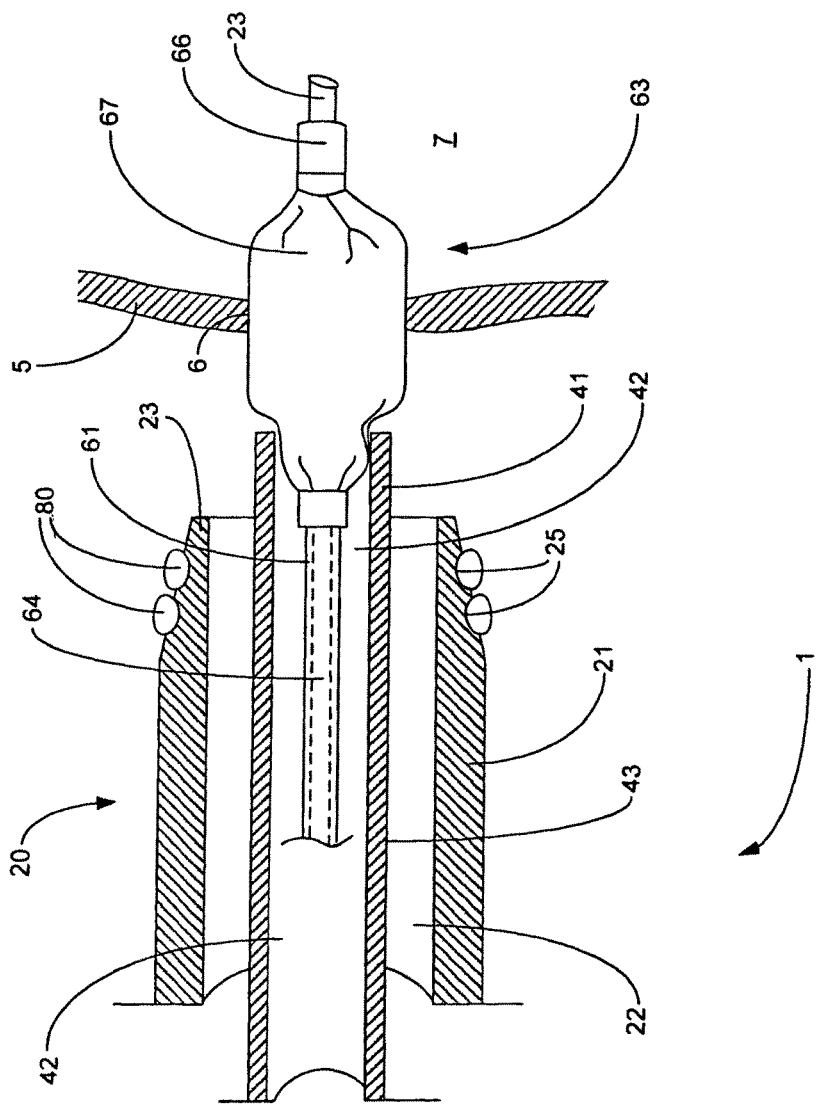
Figure 4:
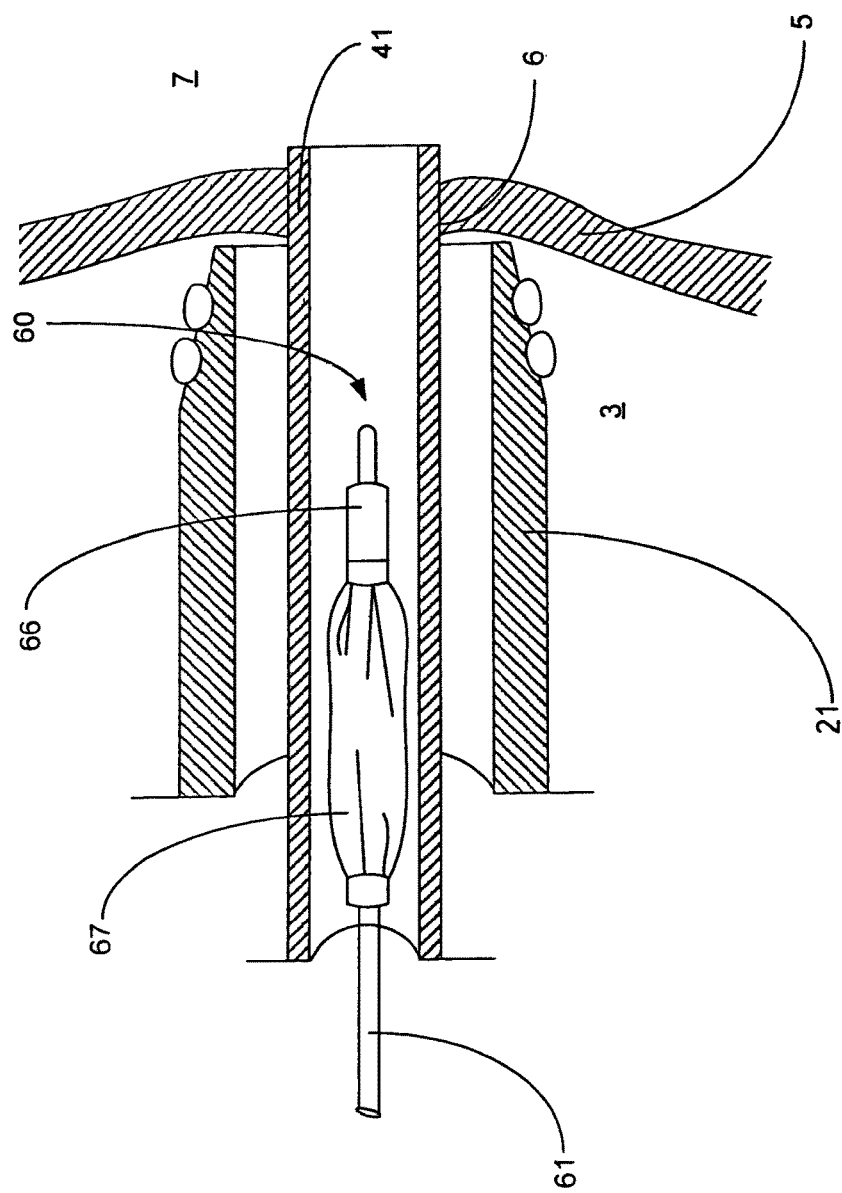

Furthermore, dilation portion 63 may be configured to be longitudinally moveable relative to and/or advanced over elongate member 61 up to distal portion 62. In some embodiments, a portion, such as, for example, distal portion 62, of elongate member 61 may include a stop mechanism 66 to prevent dilation portion 63 from advancing distally past distal portion 62, for example, as shown in FIGS. 2-4. In an alternative embodiment, however, dilation portion 63 may be advanced distally so as to surround distal portion 62, for example, so as to prevent distal portion 62 from piercing tissue or damaging a lumen of a medical instrument. Additionally, although the depicted embodiments illustrate stop mechanism 66 disposed on an external surface of elongate member 61, those having ordinary skill in the art will readily appreciate that stop mechanism 66 may be disposed internally to elongate member 61. For example, stop mechanism 66 may be wholly or partially disposed within lumen 64 of elongate member 61.

Alternatively, dilation portion 63 may be fixed relative to distal portion 62, and dilation portion 63 may be moved distally to perforation 6 by extending all of assembly 60 distally. In such a configuration, stop mechanism 66 may instead be configured to provide tactile feedback so as to provide a signal to a user that distal portion 62 has sufficiently advanced through wall 5 and into body cavity 7, for example, when stop mechanism 66 comes into contact with wall 5.

As alluded to above, dilation portion 63 may include a balloon 67. Balloon 67 may be configured to be inflated and/or deflated, for example, via fluid flow from lumen 64 with which balloon 67 may be in fluid communication. While being advanced through lumen 42 of elongate member 40, balloon 67 may be sufficiently deflated so as to allow it to be advanced therethrough (e.g., balloon 67 may have a smaller cross-sectional area than lumen 42), for example, as shown in FIG. 2. Balloon 67 may be configured to be advanced through perforation 6 in GI tract 3 that may be created by distal portion 62. Once at least a portion of balloon 67 is advanced distally past distal portion 41 of elongate member 40, balloon 67 may be configured to be inflated, for example, via fluid flow from lumen 64. Balloon 67 may have sufficient rigidity during inflation such that while disposed in perforation 6, the expansion of balloon 67 may cause the expansion of perforation 6 to any suitable size, for example, such that distal portion 41 of elongate member 40 may be advanced therethrough. Indeed, balloon 67 may expand to a size such that its cross-sectional area is larger than that of elongate member 40, and may be configured to be allowed to advance distally when distal pressure is applied to a proximal portion of balloon 67 via distal portion 41 of elongate member 40. In some embodiments, however, balloon 67 may expand to a size such that its cross-sectional area is substantially the same or slightly smaller than that of elongate member 40. Balloon 67 may then be configured to be deflated and advanced proximally out of lumen 42, lumen 22, and/or GI tract 3. Balloon 67 may be advanced and/or retracted integrally with or separately from elongate member 61 and/or distal portion 62.

Balloon 67 may have any suitable shape and/or configuration for facilitating entry into and expanding perforation 6. For example, when inflated, balloon 67 may have a substantially cylindrical configuration and a substantially circular cross-sectional shape. Balloon 67 may also have any suitable dimensions for achieving the above-discussed functions. For example, balloon 67 may have a substantially constant cross-sectional diameter along its entire length. Alternatively, balloon 67 may have a gradually increasing or decreasing cross-sectional diameter. For example, a distal portion of balloon 67 may have a smaller cross-sectional diameter than a portion disposed proximally of the distal portion.

Securing mechanism 80 may be configured to secure tissue to elongate member 40. For example, securing mechanism 80 may include one or more bands 81, 82 configured to secure wall 5 of GI tract 3 to an exterior surface 43 of distal portion 41 of elongate member 40. Bands 81, 82 may be configured (e.g., flexibly and/or elastically) such that, in a first configuration, bands 81, 82 are secured around distal portion 23 of outer housing 20 (e.g., in a tensioned state) and, in a second configuration, bands 81, 82 are secured around wall 5 of GI tract 3 which is disposed around distal portion 41 of elongate member 40 (e.g., also in a tensioned state). Bands 81, 82 may be configured to secure wall 5 to distal portion 41 with sufficient force such that when body cavity 7 is insufflated, for example, so as to provide room for a user to observe body organs and/or operate with medical instruments in body cavity 7, a fluidtight seal is maintained between wall 5 and distal portion 41 so as to prevent air from escaping from body cavity 7 into GI tract 3 via aperture 6. Bands 81, 82 may be configured to secure wall 5 to distal portion 41 with sufficient force such that movement of elongate member 40 may not cause wall 5 to be dislodged from distal portion 41. However, bands 81, 82 may be configured to allow wall 5 to detach from distal portion 41 should sufficient force be applied such that wall 5, or some other portion of GI tract 3, would not tear or be otherwise damaged due to movement of elongate member 40. Bands 81, 82 may be any suitable bands, for example, bands disclosed in U.S. Pat. No. 6,235,040, the entirety of which is incorporated herein by reference. Bands 81, 82 may be made of any suitable material, for example, silicone, butyl rubber, thermoplastics, elastomers, and/or latex. Bands 81, 82 may be configured to either be sterilized or difficult to sterilize (e.g., planned obsolescence) as desired.

Securing mechanism 80 may be disposed on distal portion 23 of outer housing 20 using any suitable method, configuration, and/or mechanism. For example, bands 81, 82 may adhere to distal portion 23 with sufficient elastic force so as to prevent bands 81, 82 from becoming detached from distal portion 23 (e.g., while outer housing 20 is being advanced down GI tract 3 to the desired location) unless sufficient proximal or distal force is applied. In another example, distal portion 23 may include one or more depressions 25 configured to accommodate one or more bands 81, 82 until sufficient radial and/or longitudinal force is applied to dislodge them.

Securing mechanism 80 may be configured to form a substantially fluidtight seal between wall 5 and distal portion 41 of elongate member 40 without severing wall 5. The elasticity of securing mechanism 80 thus may vary depending on the tissue to which securing mechanism 80 may be applied. In some embodiments, securing mechanism 80 may extend all the way around distal portion 41 and have portions of wall 5 disposed between it and distal portion 41 such that no portion of securing mechanism 80 actually comes into physical contact with exterior surface 43 of distal portion 41.

Securing mechanism 80 may be moved from distal portion 23 to secure wall 5 to distal portion 41 using any suitable method, mechanism, and/or configuration. For example, bands 81, 82 may be moved distally off of distal portion 23 and onto wall 5 and distal portion 41 by distally rolling bands 81, 82 using any suitable method or mechanism. One exemplary method may include embedding one or more strands between bands 81, 82 and distal portion 23, running both ends of the one or more strands through lumen 21, and then pulling the strands proximally so as to dislodge bands 81,82 from distal portion 23 and onto wall 5 surrounding distal portion 41. Another method may include a device for wiping or distally pushing bands 81, 82 off of distal portion 23 and onto wall 5, for example, an elongate member with a stiff distal end or a tube configured to surround outer housing 20. A further method may include using fluid pressure, for example, by running fluid through outer housing 20 to an outlet around distal portion 23 beneath bands 81, 82, to push bands 81, 82 out of depressions 25 and, due to the tapered geometry of distal portion 23, have them move distally onto wall 5.

In various embodiments, securing mechanism 80 may be any suitable mechanism configured to secure tissue to elongate member 40, for example, clips, clamps, adhesives, sutures, strands, wraps, and/or staples. Such securing mechanisms 80 may secure tissue to elongate member 40 using any suitable method, for example, mechanically and/or chemically. For example, it is contemplated that securing mechanism 80 may include one more suture loops (not shown) controllable or actuable from a remote location, such as, for example, outside a patient's body. In particular, some embodiments, may include purse-string-like suture loops that may be selectively cinched about elongate member 41.

In various embodiments, any portion of outer housing 20, elongate member 40, elongate assembly 60, and/or securing mechanism 80 may have any suitable, shape, size, and/or configuration. For example, distal portion 41 of elongate member 40 may be provided with one or more depressions or grooves (not shown) configured to receive bands 81, 82. The depressions or grooves may be disposed on an external surface of distal portion 41 and may extend partially or completely about the circumference of distal portion 41. Furthermore, any portion of outer housing 20, elongate member 40, elongate assembly 60, and/or securing mechanism 80 may be made out of any suitable biocompatible material(s) for placement in a body lumen of a patient and/or in any suitable medical device(s). Any portions of outer housing 20, elongate member 40, elongate assembly 60, and/or securing mechanism 80 may have any suitable cross-sectional shape.

Figure 10:
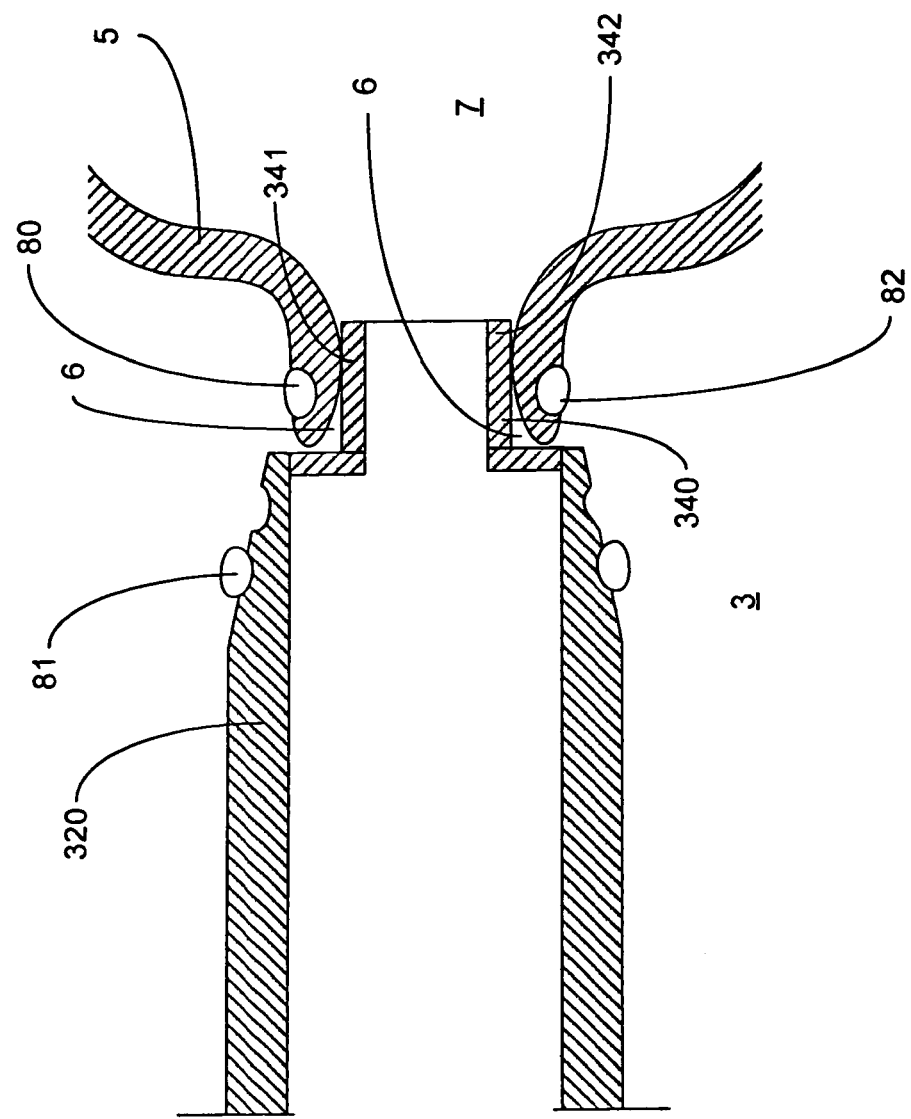
FIG. 10 depicts an apparatus, according to yet another embodiment of the invention.

In various embodiments, outer housing 20 and elongate member 40 may be connected such that they are not longitudinally moveable relative to each other and/or may be a single integrally-formed member, for example, as shown in FIG. 10. In such a configuration, distal portion 341 of elongate member 340 may extend past a distal end of outer housing 320 so as to form a lip 342 onto which wall 5 may be attached using bands 81, 82. Thus, lip 342 may have a cross-sectional area smaller than a cross-sectional area of outer housing 320 adjacent to lip 342. Outer housing 320 accordingly could not be removed from GI tract 3 once bands 81, 82 secure wall 5 to lip 342 of distal portion 341. Like distal portion 41, lip 342 may include one or more depressions or grooves (not shown) configured to receive bands 81, 82, as discussed above. Furthermore, lip 342 may have any suitable configuration for creating a seal with portions of wall 5. For example, lip 342 may be configured in the shape of a curved funnel, so that distal end of lip 342 extends radially outward to better follow the contours of wall 5 shown in FIG. 10.

An embodiment of the invention may include a method, an example of which is shown in FIGS. 1-6, 6A, and 6B. The method may include providing apparatus 1 and endoscope 2. Endoscope 2 may be advanced through a body lumen, for example, GI tract 3. At a suitable location in GI tract 3, advancement of endoscope 2 may cease, and apparatus 1 may be advanced into the body lumen, for example, GI tract 3. Apparatus 1 may be advanced into GI tract 3 via lumen 4 of endoscope 2, for example, as shown in FIG. 6B, or separate from endoscope 2. Apparatus 1 may be advanced into GI tract 3 in any suitable configuration. For example, elongate member 40 and/or elongate assembly 60 may be completely disposed within outer housing 20 such that no portion of elongate member 40 and/or elongate assembly 60 extends distally past distal portion 23 of outer housing 20. In another example, none of elongate member 40 and/or elongate assembly 60 may be disposed in outer housing 20 until outer housing 20 has been advanced to the desired location in the GI tract 3.

Once apparatus 1 has been appropriately advanced through GI tract 3, elongate assembly 60 may be distally advanced through lumen 22 and/or lumen 42 until distal portion 62 extends distally past distal portion 23. Distal portion 62 may then be advanced through wall 5 of GI tract 3 so as to create perforation 6, for example, as shown in FIG. 1. Distal portion 62 may increase in cross-sectional area as one advances proximally from the distal tip of distal portion 62. Distal portion 62 may be advanced through wall 5 until perforation 6 is the desired size, for example, by exerting pressure distally on elongate member 61. In the alternative, distal portion 62 may emit energy so as to form perforation 6 without physically contacting wall 5.

Dilation portion 63 may then be advanced over elongate member 61, for example, as shown in FIG. 2, until a distal end of dilation portion 63 comes into contact with stop mechanism 66. Alternatively, dilation portion 63 may be advanced along with elongate member 61. Balloon 67 may be in a deflated configuration while being advanced through lumen 22 and/or lumen 42 such that balloon 67 has a smaller cross-sectional area than lumen 22 and/or lumen 42. Dilation portion 63 may then be advanced with or without distal portion 62 until at least a portion of balloon 67 may be disposed in perforation 6. Perforation 6 may increase in size when deflated balloon 67 is advanced therethrough. Balloon 67 may then be inflated and expand perforation 6, for example, via fluid from lumen 64 and/or source 68. An example of expanded balloon 67 disposed in perforation 6 is shown in FIG. 3. When balloon 67 has been inflated such that perforation 6 has the desired cross-sectional area, balloon 67 and/or distal portion 62 may be advanced through perforation 6, for example, via distal pressure on a proximal portion of balloon 67 exerted by distal portion 41 of elongate member 40. Distal portion 62, dilation portion 63, and/or elongate member 40 may be advanced through perforation 6 until a sufficient amount of distal portion 41 is disposed within perforation 6, for example, to allow securing mechanism 80 to sufficiently secure enough of wall 5 to exterior surface 43. To that end, inflated balloon 67 may have a cross-sectional area equal to or greater than a cross-sectional area of distal portion 41. Balloon 67 may then be deflated using any suitable method, for example, via suction from lumen 64 connected to source 68, and then elongate assembly 60 may be advanced proximally and removed from GI tract 3 via lumen 22 and/or lumen 42. Such an example is shown in FIG. 4.

Figure 5:
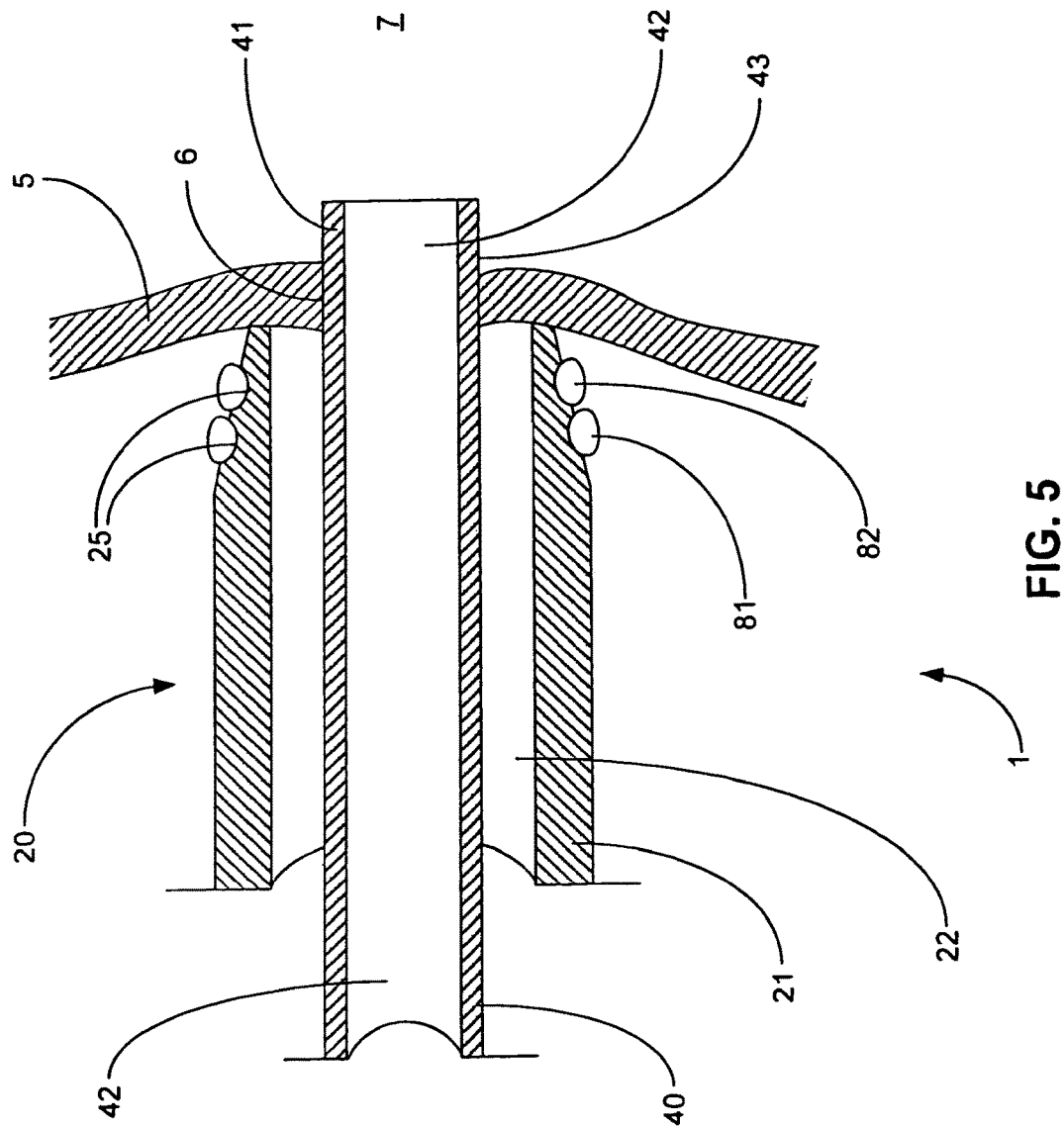

With distal portion 41 of elongate member 40 disposed in perforation 6, outer housing 20 and/or elongate member 40 may be advanced distally so as to place wall 5 under a sufficient amount of tension to aid in the placement of securing mechanism 80, for example, as shown in FIG. 5. Lumen 22 of outer housing 20 may also create suction so as to draw or pull some of wall 5 into the portion of lumen 22 defined by distal portion 23. In addition to utilizing suctioning forces to draw portions of wall 5 into lumen 22, those of ordinary skill in the art will readily recognize that tissue may be pulled into lumen 22 by any other means known in the art.

Under such tension, securing mechanism 80 may be advanced from a position about distal portion 23 of outer housing 20 so as to secure wall 5 to exterior surface 43 of elongate member 40 using any suitable method. For example, a medical instrument 100 may exert radially outward and/or distal pressure on bands 81, 82 so as to dislodge bands 81, 82 from depressions 25 and advance them distally past distal portion 23. As bands 81, 82 are advanced distally, bands 81, 82 may come into contact with wall 5. When such contact occurs, outer housing 20 may be advanced proximally. Such proximal movement may cause bands 81, 82 to advance distally past distal portion 23 and onto wall 5. Bands 81, 82 may contract so as to cause wall 5 to be secured to exterior surface 43 of distal portion 41 of elongate member 40, for example, as shown in FIG. 6. In some embodiments, to facilitate securing wall 5 to distal portion 41, lumen 42 of elongate member 40 may be provided with suction to pull portions of wall 5 toward distal portion 41. For example, it is contemplated that distal portion 41 may be provided with a plurality of through holes (not shown) in the wall of elongate member for fluidly communicating lumen 42 with exterior surface 43. The holes would allow the suction force within lumen 42 to act upon portions of wall 5 to draw portions of wall 5 toward exterior surface 43. Once wall 5 is secured to exterior surface 43 of distal portion 41, outer housing 20 may then be removed from GI tract 3, leaving elongate member 40 secured to wall 5 via securing mechanism 80.

One or more medical devices may then be advanced through GI tract 3 via lumen 42, past wall 5, and into body cavity 7, for example, that may include one or more internal body organs. The one or more medical devices may then be used to perform any medical procedure on any body portion (e.g., treat, explore, and/or acquire tissue samples from internal body organs and/or tissue) and, once finished, the one or more medical devices may be removed from body cavity 7 and/or GI tract 3 via lumen 42. Once all medical procedures have been completed, bands 81, 82 may be removed from wall 5 using any suitable method and all portions of apparatus 1 may be removed from GI tract 3 and body cavity 7. Perforation 6 may then either be allowed to naturally heal or perforation 6 may be closed using any suitable method, for example, sutures.

In an alternative embodiment, outer housing 20 may be left in GI tract 3 surrounding elongate member 40 while medical procedures are being performed in body cavity 7 and, once the procedures have been completed, outer housing 20 may be used to strip bands 81, 82 from distal portion 41 of elongate member 40. In a further embodiment, bands 81, 82 may be cut, for example, using a knife or a device that cuts using energy.

In yet another alternative embodiment, elongate member 40 may be pulled out of perforation 6 in wall 5, causing bands 81, 82 to remain around portions of wall 5 and close perforation 6. In particular, it is contemplated that once elongate member 40 is pulled out of perforation 6, at least one of bands 81, 82 may contract about portions of wall 5 that are proximate perforation 6, so as to close perforation 6. Bands 81, 82 may contract by any suitable means known in the art. For example, bands 81, 82 may elastically contract about portions of wall 5. In another example, bands 81, 82 may include an actuator, such as, for example, a drawstring or a purse string, for mechanically contracting bands 81, 82 about portions of wall 5. In yet another example, bands 81, 82 may be made of temperature sensitive material that may be configured to contract in response to an increase or decrease in temperature. Additionally, it is contemplated that bands 81,82 may be made of a biodegradable materials, so as to degrade within a patient's body after perforation 6 has been permanently closed by the body's healing response.

At any point in the procedure, irrigation and/or aspiration may be conducted through one or more of lumens 22, 42 from respective source of fluid or suction 26, 44.

Another embodiment of the invention may include using apparatus 1 to close an aperture, such as, for example, an incision or access site, in a wall 5 of tissue. In particular, it is contemplated that elongate member 21 may be advanced towards a aperture, such as, for example, perforation 6, until distal portion 23 may be disposed proximate perforation 6. In some instances, the portions of wall 5 surrounding perforation 6 may be pulled into lumen 22 to facilitate closing perforation 6. The portions of wall 5 surrounding perforation 6 may be pulled into lumen 22 by any suitable means known in the art. For example, suction may be applied to lumen 22 so as to draw some of wall 5 into a portion of lumen 22. Subsequently, securing mechanism 80, such as, for example, bands 81, 82 may be advanced from a position about distal portion 23 so as to contract about portions of wall 5 that are proximate perforation 6, thereby closing perforation 6.

In various embodiments, apparatus 1 may be used in conjunction with any suitable body organ and/or body tissue. Apparatus 1 may be used in conjunction with any suitable medical device and/or any suitable medical procedure, for example, any transoral, transanal, and/or transvaginal medical procedure. Some exemplary procedures may include natural orifice transluminal endoscopic surgery, obesity procedures, cholestectomy, gynecologic procedures, appendectomy, cardiac surgery procedures, lung surgery, and/or urologic procedures.

Once tissue has been secured to apparatus 1, one or more medical devices may be advanced through any portion of apparatus 1 and through perforation 6 into any suitable body lumen and/or body cavity to perform any suitable medical procedure. Examples of medical devices may include endoscopes, robotic instruments, catheters, lapropscopic instruments, optical tools, and/or biopsy tools.

There are various advantages to the use of apparatus 1 and related methods. For example, because perforations 6 are disposed inside the body in GI tract 3, perforations 6 that are appropriately sealed are not exposed to the outside environment, and thus contamination risks are reduced. In another example, because perforations 6 are made in GI tract 3, or some other body lumen, it is possible to locate perforations 6 closer to at least some internal body organs in body cavity 7 to be treated then via laproscopic procedures. This may aid in preventing trauma and/or damage to other body organs by minimizing the number of body organs the medical devices must be placed through and/or around in order to reach the body organ to be treated. In a further example, because perforations 6 are located in the GI tract 3, smaller incisions may be made as compared to other procedures, reducing scarring, recovery time, and pain to the patient. In another example, by passing medical devices through lumen 42 of elongate member 40, contamination of the medical devices from contact with the GI tract 3 or other body lumen may be minimized. In a further example, by creating a substantially fluidtight seal between distal portion 41 of elongate member 40 and wall 5, when advancing fluid into body cavity 7 so as provide insufflation, leakage of such fluid from body cavity 7 to GI tract 3 may be minimized. Minimizing such leakage may be desirable, for example, to allow a user to view body cavity 7 and provide enough space to perform medical procedures without constantly running more fluid to body cavity 7 to maintain insufflation.

Figure 7:
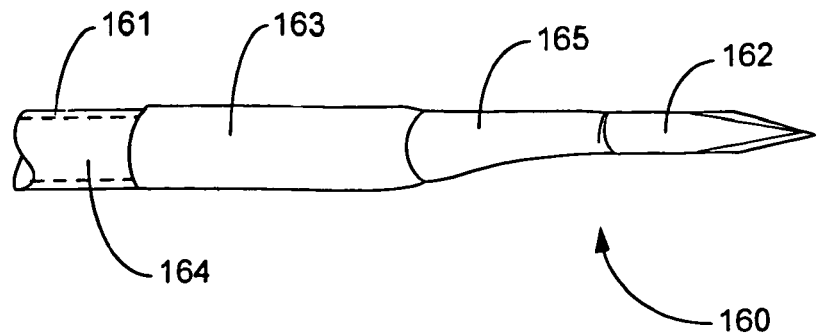
FIGS. 7-8 depict an apparatus, according to another embodiment of the invention.
Figure 8:
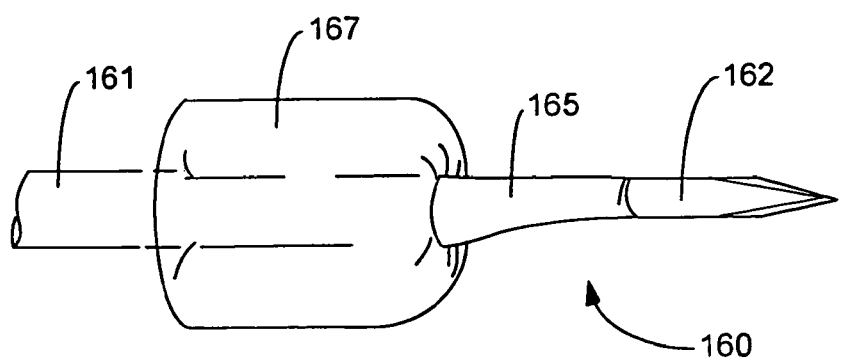

Another example of an elongate assembly 160 is shown in FIGS. 7-8. Elongate assembly 160 may include an elongate member 161, a distal portion 162, and a dilation portion 163. Elongate assembly 160 may be configured to be advanced through one or more lumens of one or more medical devices, for example, lumen 22 of outer housing 20 and lumen 42 of elongate member 40. Elongate assembly 160 may be configured to be advanced through a body lumen, for example, GI tract 3. Elongate member 161 may define a lumen 164 configured to accommodate fluid flow therethrough, for example, suction or irrigation of any suitable liquid or gas.

Distal portion 162 may have any combination of the aspects set forth herein for distal portion 62. Generally, distal portion 162 may be configured to pierce tissue, for example, wall 5 of GI tract 3.

Dilation portion 163 may also have any combination of the aspects set forth herein for dilation portion 63, for example, a balloon 167 substantially similar to balloon 67. Balloon 167 may be in flow communication with a source of fluid to inflate balloon 167 via lumen 164. Generally, dilation portion 163 may be configured to be inflated to any desired size. However, unlike distal portion 62 and dilation portion 63, dilation portion 163 is longitudinally fixed relative to distal portion 162.

A transition portion 165 may be disposed between distal portion 162 and dilation portion 163. Transition portion 165 may have a gradually tapering cross-sectional area between distal portion 162 and dilation portion 163. For example, a proximal end of transition portion 165 may be configured to have substantially the same cross-sectional area as a distal end of dilation portion 163 when dilation portion 163 is in an uninflated state. In another example, a distal end of transition portion 165 may be configured to have substantially the same cross-sectional area as a proximal end of dilation portion 162. Transition portion 165 may be configured to gradually expand aperture 6 as elongate assembly 160 is gradually advanced through aperture 6 and into body cavity 7.

Figure 9:
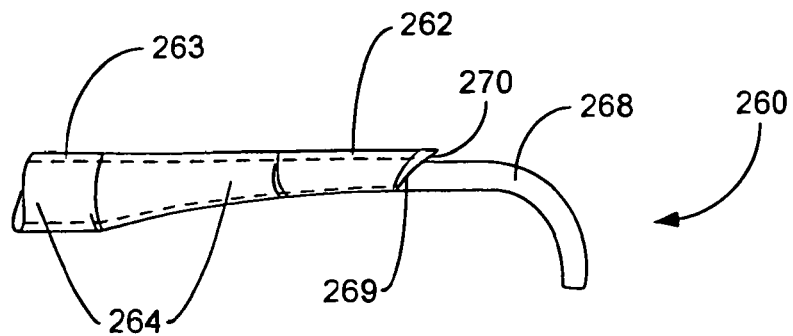
FIG. 9 depicts an apparatus, according to a further embodiment of the invention.

Another example of an elongate assembly 260 is shown in FIG. 9. Elongate assembly 260 may include a distal portion 262, a dilation portion 263, and an elongate member 268. Elongate assembly 260 may be configured to be advanced through one or more lumens of one or more medical devices, for example, lumen 22 of outer housing 20 and lumen 42 of elongate member 40. Elongate assembly 260 may be configured to be advanced through a body lumen, for example, GI tract 3.

Distal portion 262 may be configured to pierce tissue, for example, wall 5 of GI tract 3. Such tissue pierce may be achieved by a sharp distal edge 270 of distal portion 262.

Distal portion 262 may define a lumen 264 including any combination of aspects set forth above with respect to lumens 64, 164. A distal end 269 of lumen 264 may be configured to be in flow communication with the outside environment. Furthermore, lumen 264 may be configured to accommodate elongate member 268 therethrough, for example, a guidewire. Elongate member 268 may be deployed out of distal end 269 of lumen 264 at any point in time, for example, when distal end 269 of lumen 264 is disposed in body cavity 7. Once elongate member 268 has been deployed in body cavity 7, aperture 6, and/or GI tract 3, the rest of elongate assembly 260 may be removed and elongate member 268 may be utilized with any suitable medical device using any suitable method.

Dilation portion 263 may also have any combination of the aspects set forth herein for dilation portions 63, 163, for example, dilation portion 263 may be in flow communication with lumen 264. Generally, dilation portion 263 may be configured to be inflated to any desired size.

In any apparatus and/or method set forth herein, elongate assemblies 60, 160, 260 are interchangeable insofar as each of elongate assemblies 60, 160, 260 is physically compatible with the rest of the apparatus and/or structurally capable of performing the recited method step.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method, comprising:
    advancing an outer housing defining a first lumen through a body lumen;
    advancing an elongate member defining a second lumen through the first lumen;
    forming a perforation in a wall of the body lumen;
    advancing a distal portion of the elongate member through the perforation;
    securing body tissue surrounding the perforation to the distal portion of the elongate member with a securing mechanism; and
    after securing the body tissue, removing the outer housing from the body lumen.

2. The method of claim 1, further comprising advancing the securing mechanism from the outer housing to the body tissue surrounding the distal portion of the elongate member so as to secure the body tissue to the distal portion of the elongate member.

3. The method of claim 1, further comprising contracting the securing mechanism around the body tissue surrounding the distal portion of the elongate member so as to secure the body tissue to the distal portion of the elongate member.

4. The method of claim 1, further comprising longitudinally moving the outer housing and the elongate member relative to each other.

5. The method of claim 1, wherein the securing mechanism is configured to form a seal between the tissue and the distal portion of the elongate member.

6. A method, comprising:
    advancing an elongate assembly into a body lumen, the elongate assembly including a distal portion and a dilation portion;
    longitudinally moving the distal portion of the elongate assembly and the dilation portion relative to each other;
    forming a perforation in a wall of the body lumen by piercing the wall with the distal portion of the elongate assembly;
    advancing the dilation portion into the perforation;
    expanding the perforation by activating the dilation portion;
    after expanding the perforation, advancing a distal portion of an elongate member defining a lumen into the perforation; and
    securing body tissue surrounding the perforation to the distal portion of the elongate member with a securing mechanism.

7. The method of claim 6, further comprising positioning an outer housing over the elongate assembly proximate the perforation; and
    moving the securing mechanism from the outer housing to the body tissue surrounding the distal portion of the elongate member so as to secure the body tissue to the distal portion of the elongate member.

8. The method of claim 6, further comprising sealing the body tissue surrounding the perforation to the distal portion of the elongate member with the securing mechanism.

9. The method of claim 6, wherein a lip is disposed on the distal portion of the elongate assembly and configured to accommodate a tissue thereon, the lip having a cross-sectional area smaller than a cross-sectional area of a second portion of the distal portion of the elongate assembly adjacent and proximal to the lip.

10. The method of claim 6, further comprising, after the step of expanding the perforation, removing the dilation portion from the body lumen.

11. A method, comprising:
    providing a first elongate member proximate an aperture in a wall of tissue, wherein the first elongate member includes a lumen and a securing mechanism;
    providing a second elongate member disposed within the lumen of the first elongate member and extending through the aperture;
    pulling tissue surrounding the aperture toward the first elongate member, wherein pulling the tissue includes suctioning the tissue; and
    deploying the securing mechanism about the tissue surrounding the aperture to secure the tissue surrounding the aperture to the second elongate member.

12. The method of claim 11, wherein pulling tissue surrounding the aperture toward the first elongate member includes pulling tissue into the lumen of the first elongate member.

13. The method of claim 11, further comprising, after the step of deploying the securing mechanism, removing the first elongate member from a patient body including the tissue.

14. The method of claim 11, wherein the securing mechanism is configured to form a seal between the tissue and the second elongate member.

15. The method of claim 11, further comprising inserting a medical device through a lumen within the second elongate member.

* * * * *